United States Patent [19]

Matza et al.

[11] E Patent Number: Re. 33,349

[45] Reissued Date of Patent: Sep. 25, 1990

[54] CONTROLLING SULFIDE SCAVENGER CONTENT OF DRILLING FLUID

[75] Inventors: Stephen D. Matza, Stafford; William E. Ellington; Henry C. Fleming, III, both of Houston, all of Tex.

[73] Assignee: Shell Oil Company, Houston, Tex.

[21] Appl. No.: 158,828

[22] Filed: Feb. 19, 1988

Related U.S. Patent Documents

Reissue of:

[64] Patent No.: 4,658,914
Issued: Apr. 21, 1987
Appl. No.: 784,422
Filed: Oct. 4, 1985

U.S. Applications:

[63] Continuation-in-part of Ser. No. 609,611, May 14, 1984, abandoned.

[51] Int. Cl.[5] ..... E21B 44/00; E21B 47/10; G01N 31/02; G01N 33/24

[52] U.S. Cl. ..... 175/40; 175/64; 436/25; 436/81; 436/120; 436/178

[58] Field of Search ..... 436/81, 119, 120, 25, 436/175, 174; 175/64, 40

[56] References Cited

U.S. PATENT DOCUMENTS 3,706,532 12/1972 Noll ..... 436/175 X
3,928,211 12/1975 Browning et al. ..... 175/64 X
4,252,655 2/1981 Carney ..... 175/64 X

OTHER PUBLICATIONS

Calmer, Steven H., "$H_2S$ Detector Aids Drilling Safety, Data", *Oil & Gas Journal*, Nov. 19, 1979, pp. 160–163.

Carney, Leroy L., and Jones, Bob, "Practical Solutions to Combat the Detrimental Effects of Hydrogen Sulfide During Drilling Operations", 1974, Society of Petroleum Engineers of AIME, Paper No. SPE 5198.

Garrett, R. L., "A New Field Method for the Quantitative Determination of Sulfides in Water-Base Drilling Fluids", *Journal of Petroleum Technology*, Sep., 1977, pp. 1195–1202.

Khristoforov et al., Chemical Abstracts, vol. 72, 1970, No. 96393r.

Sandell, "Colorimetric Determination of Traces of Metals", Interscience Publishers, Inc., New York, 1944, pp. 449–450.

The Condensed Chemical Dictionary, Tenth Edition, Van Nostrand Reinhold Co., New York, 1981, pp. 1106–1113.

Garrett et al., Journal of Petroleum Technology, Jun. 1979, pp. 787–796.

*Primary Examiner*—Robert J. Warden
*Assistant Examiner*—Jill Johnston

[57] ABSTRACT

The concentration of unspent zinc-based hydrogen sulfide scavenger in an aqueous drilling fluid is controlled by selectively extracting the unspent scavenger in a solvent, such as glacial acetic acid, measuring the concentration of dissolved zinc, for example, with an X-ray fluorescence spectrograph, and utilizing the results of the measurements to proportion the extent of changes to be made in the concentration of the scavenger.

11 Claims, No Drawings

CONTROLLING SULFIDE SCAVENGER CONTENT OF DRILLING FLUID

Matter enclosed in heavy brackets [ ] appears in the original patent but forms no part of this reissue specification; matter printed in italics indicates the additions made by reissue.

RELATED PATENT APPLICATION

This is a continuation-in-part of patent application Ser. No. 609,611 filed May 14, 1984, now abandoned, the disclosures of which are incorporated herein by reference.

BACKGROUND OF THE INVENTION

The present invention relates to determining and utilizing the amount of unspent zinc-based sulfide scavenger which is present in a water-based drilling fluid for adjusting the scavenging capability of the drilling fluid to the extent desired during the drilling of a well. More particularly, the invention relates to a relatively quick and accurate procedure which can be used in field locations.

A state of the art paper entitled "Chemical Scavengers for Sulfides in Water-Based Drilling Fluids" by R. L. Garrett, R. K. Clark, L. L. Carney and C. K. Grantham, Sr. in Journal of Petroleum Technology, June 1979, page 787, discusses the chemistry of commercial scavengers for water-based drilling fluids, the parameters that affect the reliability of such materials and the problems affecting scavenger use. On page 796, the authors point out that "From this state of the art review one can see that we believe more research is needed to develop scavengers and tests for scavenger content in muds that match more closely the qualities of an ideal scavenger."

U.S. Pat. No. 3,706,532 describes a method for determining zinc concentrations in aqueous mediums. A sample mediums is acidified, treated with a buffered complexing agent to complex aluminum or iron ions, treated with an organo sulfur compound to complex copper ions, then analyzed by adding an indicator the color intensity of which is calibrated with respect to known concentrations of zinc. U.S. Pat. No. 3,928,211 describes a class of zinc carbonate, basic zinc carbonate and zinc hydroxide compounds effective for sulfide scavenging. U.S. Pat. No. 4,252,655 describes the removal or inactivation of hydrogen sulfide contamination by adding at least one organic zinc chelate.

SUMMARY OF THE INVENTION

The present invention relates to improving a process for drilling a well with an aqueous drilling fluid containing a zinc-based scavenger of sulfide ions. A determination is made of the amount of unspent zinc-containing sulfide-scavenging material present in the drilling fluid. A measured volume of the drilling fluid is mixed with a significantly larger number of volumes (such as about 6 to 10) of a selective solvent for dissolving zinc ions and establishing within the resulting mixture a pH (such as a pH of from about 4 to 6) at which substantially all of the zinc in the drilling fluid, except for that combined into zinc sulfide molecules, becomes dissolved in the liquid phase of the mixture. A portion of the resulting liquid solution is separated from the solid components of the drilling fluid and the amount of zinc contained in the solids-free liquid is determined in order to determine the amount of unspent zinc-containing sulfide scavenger in the drilling fluid. The amount of scavenger in the mud is then adjusted to the extent required to provide a capability of precipitating a selected amount of sulfide ions without involving a solids content capable of impairing the drilling fluid rheology.

In a preferred embodiment of the invention the drilling fluid sample is mixed with about 4 to 10 times its volume of glacial acetic acid, or a selective solvent which is substantially equivalent to glacial acetic acid with respect to selectively dissolving zinc ions which have not combined with sulfide ions. The concentration of zinc in the resulting solution is preferably measured with a portable X-ray fluorescence spectrographic unit which is, or is substantially equivalent to, a Portaspec Model 2501 portable X-ray spectrograph (available from Pitchford Scientific Instruments Division of the Hankison Corporation).

In a preferred procedure, for example, in situations in which the proportions found of unspent zinc based scavenger are relatively low, an augmentive test for total zinc (including that combined into zinc sulfide molecules) can be performed by (a) an X-ray fluorescence measurement, or equivalent measurement, of the zinc in the unleached drilling fluid or, (b) using as the solvent for dissolving zinc from the drilling fluid a strong acid, such as hydrochloric acid, as a solvent, for combined and non-combined zinc, prior to measuring the concentration of the zinc solution. Such an acid preferably has a normality of from about 1 to 3. The difference between the prior and augmentive tests will indicate whether the scavenger concentration was reduced by dilution of the drilling fluid or by combination with sulfide.

DESCRIPTION OF THE INVENTION

Applications have discovered that possible needs for changing the concentration of zinc base scavenger in a drilling fluid can be accurately monitored at the well site so the corrections in the rate of scavenger addition can be properly initiated. This can be effected by utilization of the present process. This process enables the drilling fluid to be sampled at a selected frequency with the results of determinations of the concentrations of unspent scavenger promptly available to the mud engineers. For example, within about 30 minutes or so, based on such information, increases or decreases can be made in the rate of scavenger addition and for additions of scavenger-free fluid to the extent needed to quickly change that concentration to either avoid an impairment of the drilling fluid rheology or to quickly scavenge a sudden encounter or sulfide.

Experiments were conducted using samples of an aqueous drilling fluid typical of that used in drilling operations. Quadruplicate examples were performed on samples of that mud spiked with proportions of 1 lb. per barrel (ppb) of Sulf-X (a zinc based sulfide scavenger available from Imco Services, a Halliburton Company). The tests employed the following procedures, which are preferred procedures for use in the present invention.

SAMPLE PREPARATION

1. Measure 10 ml of stirred mud into a 10 ml graduated cylinder using a pipet with the end of the pipet cut off to minimize any particle size exclusion.

2. Transfer the measured mud sample to a 150 ml beaker.
3. Add 60 ml of glacial acetic acid to the mud sample.
4. Heat at about 110° C. with frequency stirring for 10–15 minutes.
5. Allow the solution to cool sufficiently to prevent damage to a plastic centrifuge tube.
6. Place a portion of the mud-acetic acid mixture into a plastic 50 ml centrifuge tube.
7. Centrifuge so that all the mud is firmly packed at the bottom of the centrifuge tube.
8. Accurately pipet 10 ml of the centrifuge solution into a Chemplex X-ray fluorescence counting vial using a 5 ml Finnpipette.
9. Cover the counting vial with polypropylene film, brace the film onto the vial with a small collar, and fix the film onto the vial with a large collar.

INSTRUMENTAL MEASUREMENTS BY X-RAY FLUORESCENCE

1. Position the element selector to Zn using the sidearm lever.
2. Open the sample compartment door.
3. Plug into a 110V outlet and engage "Power" button. Wait for the "ready" light and let warm 10 minutes.
4. Place sample counting vials in the spring-loaded mount. Insert the mount into the sample chamber with the rounded edge of the stainless mount facing inward. [Note: Make sure no droplets are present on the undersurface of the polypropylene film. These droplets will cause an errant increase in count rate.]
5. Close the sample chamber door and check to see if the "X-rays on" indicator is illuminated. If it is not illuminated, the stainless planchet holder should be reinserted in the other direction.
6. With "X-rays on", adjust the current to read 0.5 milliamps.
7. Set the counting scaler on the front panel to 60 seconds.
8. Engage count pushbutton and record the final gross X-ray intensity counts on the digital readout.
9. Obtain gross X-ray counts for the glacial acetic acid blank and a calibration standard prepared y the dissolution of ZnO in glacial acetic acid.
10. To leave instrument in standby position, open the sample compartment door.
11. For longer periods of inactivity, turn down the current, turn off main power and unplug.

CALCULATIONS (based on the following conditions)

10 ml mud, 60 ml acetic acid, 10 ml aliquots in counting vial.

Calculations are not valid for variations from these amounts.

1. Determine net counts for samples and ZnO calibration standard by subtracting the glacial acetic acid blank counts.
2. Determine the mg of Zn in 10 ml mud sample by the following ratio:

$$\text{mg Zn in 10 ml mud} = \frac{\text{Net intensity}_{sample}}{\text{Net intensity}_{Std}} \times \text{mg Zn}_{Std}$$

3. Determine ppb (pounds per barrel) Zn by multiplying the mg Zn in the 10 ml mud sample by 0.035. The factor 0.035 is derived from the following conversion:

$$\frac{\text{lb Zn}}{\text{bbl mud}} = \frac{\text{mg Zn}}{\text{10 ml mud}} \times \frac{\text{1000 ml}}{\text{1 l}} \times \frac{\text{3.79 l}}{\text{1 gal}} \times \frac{\text{42 gal}}{\text{1 bbl}} \times \frac{\text{1 g}}{\text{1000 mg}} \times \frac{\text{1 lb}}{\text{454 g}}$$

4. Determine ppb Sulf-X by multiplying ppb Zn by 1.67 [Sulf-X contains 60.0% Zn].

TEST RESULTS

The tests indicated the following:

Sulf-X was experimentally determined to be present at 0.97±0.09 ppb. These results indicate the accuracy and precision of the method to be within the 10 percent relative objective.

Additional experiments were designed to simulate situations where the scavenger containing mud had been totally exhausted by hydrogen sulfide intrusion. This was accomplished by spiking mud with 1 ppb zinc sulfide which is the product from the reaction of the zinc scavenger with sulfide. Duplicate analyses yielded unspent scavenger concentrations of 0.02±0.01 ppb indicating that the acetic acid leach is effective at differentiating spent and unspent zinc scavenger.

In a third experiment, unspiked mud was found to have 0.03 ppb unspent zinc scavenger which indicates that potential interferents inherent to the mud are virtually non-existent.

In general, the selective solvent for zinc ions can comprise substantially any buffered liquid having a composition and concentration capable of providing a pH of about 4 to 6 when one part by volume of a drilling fluid having a pH in the range of from about 9 to 12 is mixed with about 4 to 10 parts by volume of said liquid. Examples of suitable selective solvent solutions include: glacial acetic acid, 10% formic acid, and 0.0001 M hydrochloric acid.

In general, the concentration of zinc which becomes dissolved in the selective solvent can be measured by substantially any suitably accurate procedure. Procedures capable of being conducted in field locations are preferred. An example of such a procedure is described in "Colorimetric Determinations of Elements" by G. Charlot, Elsevier Publishing Company, 1964.

Suitable Compositions and Procedures for Use in the Invention

The present invention is applicable to substantially any process for drilling the borehole of a well with an aqueous drilling fluid in a location in which the wellbore may encounter water soluble sulfide ions such as those in hydrogen sulfide or salts containing $HS^-$ or $S^{\ddot{V}}$. Such acids and salts commonly coexist in a subterranean sulfide-containing water system.

In a preferred embodiment of the invention, the above described analyses are conducted at the drilling site with a frequency which increases with the likelihood of the borehole encountering sulfide ions and/or increases in the extent by which the zinc-based scavenger is found to have been depleted by round trips of the circulating drilling fluid. The zinc-based sulfide scavengers are generally available as solids and can be added as dry solids through a hopper for mixing solids with the circulating drilling fluid. But, in a preferred procedure, the scavengers are preferably added in the form of slurries in aqueous liquids. In addition, as known in the art, a lignosulfonate treatment of the drilling fluid can be utilized for controlling any undesirable zinc-induced flocculation of mud components.

In general, the most commonly used zinc based sulfide scavenger is a basic zinc carbonate. It is a manufactured compound having a formula averaging about $3Zn(OH)_2 \cdot 2ZnCO_3$. As known in the art, where desirable to minimize any adverse effects of zinc ions, those ions can be loosely bonded with organic compounds into the form of metal chelates. Commercially available zinc chelates are based on aliphatic amino acids or their salts. Such chelated zinc ions tend to avoid being captured on clay surfaces in a manner causing flocculation while still being available for precipitating sulfide ions.

What is claimed is:

1. In a process for drilling a well with a water based drilling fluid containing zinc based scavengers for controlling encountered sulfide ions, in which process analyses are made for monitoring and controlling the amount of scavenger in the drilling fluid, an improved process for controlling the adequacy of the scavenging capability, comprising:

mixing one part by volume of a sample of circulating drilling fluid with about 4 to 10 parts by volume of a selective solvent for zinc ions, with said solvent [containing a kind and amount of buffering material] providing a pH of about 4 to 6, and being capable of dissolving substantially all of the zinc present in the drilling fluid except for zinc ions combined into [precipitated molecules of] zinc sulfides;

separating the resulting solution from undissolved solids;

determining the amount of zinc in the solids-free solution in order to determine the proportion of the unspent zinc based sulfide scavenger in the circulating drilling fluid; and adjusting the proportion of the scavenger in the drilling fluid to the excent required to provide enough for scavenging a selected amount of encountered sulfide ions without providing enough to impair the rheology of the drilling fluid.

2. The process of claim 1 in which the amount of zinc in the solution is determined by measuring the amount of X-ray fluorescence exhibited by the solution.

3. The process of claim 1 in which the selective solvent for zinc is glacial acetic acid.

4. The process of claim 1 in which the selective solvent for zinc is glacial acetic acid, the mixture of drilling fluid and selective solvent contains about 1 part by volume of the drilling fluid per 4 to 10 parts by volume of the solvent and the amount of zinc which becomes dissolved in that solution is determined by a measurement of X-ray fluorescence.

5. The process of claim 1 in which an additional portion of the same drilling fluid is similarly mixed with solvent consisting of an aqueous strong acid solution capable of dissolving substantially all combined and non-combined zinc in the drilling fluid, with the amount of zinc in the solution being similarly measured to determine the decrease in scavenger due to drilling fluid dilution and reaction of scavenger with sulfides.

6. The process of claim 5 in which the strong acid is hydrochloric acid having a normality of about 1 to 3.

7. The process of claim 1 in which the amount of zinc dissolved in the selective solvent for zinc ions is determined by colorimetric analysis.

8. The process of claim 1 in which the zinc-based sulfide scavenger is a basic zinc carbonate.

9. The process of claim 1 in which the zinc-based sulfide scavenger is a water soluble zinc chelate.

10. The process of claim 1 in which determinations of the proportion of unspent zinc-based scavenger are (a) initiated at a frequency which provides a rate of testing that varies with variations in the likelihood of the borehole encountering changed sulfide ion concentrations which change the extent to which the amount of unspent scavenger is different between the tests, (b) are conducted at the drill site and, (c) to the extend required are utilized to proportion changes in the concentration of scavenger in the drilling fluid for keeping that concentration high enough to scavenge the sulfide being encountered without becoming high enough to impair the drilling fluid rheology.

11. In a process for drilling a well with water based drilling fluid containing zinc-based scavengers for controlling encountered sulfide ions in which process analyses are made for monitoring and controlling the amount of scavenger in the drilling fluid, an improved process for controlling the adequancy of the scavenging capability, comprising:

mixing one part by volume of a sample of circulating drilling fluid with about 4 to 10 parts by volume of a selected solvent for zinc ions with said solvent containing, glacial acetic acid and in an amount providing a pH of about 4 to 6, said solvent being capable of selectively dissolving zinc ions which have not combined with sulfide ions and being capable of dissolving substantially all of the zinc present in the drilling fluid except for zinc ions combined into [precipitated] molecules of zinc sulfides;

separating the resulting solution from undissolved solids;

determining the amount of zinc in the solids free solution by measuring the concentration of said zinc ions by X-ray fluorescence to determine the concentration of unspent zinc-based sulfide scavenger in the circulating drilling fluid; and adjusting the proportion of said scavenger to the extent required to provide enough for scavenging a selected amount of encountered sulfide ions without providing enough to impair the rheology of the drilling fluid.

* * * * *